(12) United States Patent
O'Prey et al.

(10) Patent No.: US 8,574,155 B2
(45) Date of Patent: Nov. 5, 2013

(54) EXPANDABLE SURGICAL ACCESS PORT

(75) Inventors: Cormac O'Prey, Bishops Stortford (GB); Valerie Anne Scott, Cambridge (GB); Simon Roderick Grover, Cambridge (GB)

(73) Assignee: Covidien LP, Mansfield, MA (US)

( * ) Notice: Subject to any disclaimer, the term of this patent is extended or adjusted under 35 U.S.C. 154(b) by 163 days.

(21) Appl. No.: 13/005,622

(22) Filed: Jan. 13, 2011

(65) Prior Publication Data

US 2011/0201896 A1    Aug. 18, 2011

Related U.S. Application Data

(60) Provisional application No. 61/304,131, filed on Feb. 12, 2010.

(51) Int. Cl.
*A61B 1/32* (2006.01)

(52) U.S. Cl.
USPC ........................................... 600/228

(58) Field of Classification Search
USPC ................................. 600/201–235
See application file for complete search history.

(56) References Cited

U.S. PATENT DOCUMENTS

| | | | |
|---|---|---|---|
| 1,780,912 A | 11/1930 | Gau | |
| 1,810,466 A | 6/1931 | Deutsch | |
| 2,313,164 A | 3/1943 | Nelson | |
| 2,541,516 A | 2/1951 | Ivory et al. | |
| 2,812,758 A | 11/1957 | Blumenschein | |
| 3,782,370 A | 1/1974 | McDonald | |
| 3,807,393 A | 4/1974 | McDonald | |
| 3,965,890 A | 6/1976 | Gauthier | |
| 4,130,113 A | 12/1978 | Graham | |
| 4,263,899 A | 4/1981 | Burgin | |
| 4,328,899 A * | 5/1982 | Krusche | 211/41.6 |
| 4,553,537 A | 11/1985 | Rosenberg | |
| 5,007,900 A | 4/1991 | Picha et al. | |
| 5,052,374 A | 10/1991 | Alvarez-Jacinto | |
| 5,080,088 A | 1/1992 | LeVahn | |
| 5,125,396 A | 6/1992 | Ray | |
| 5,169,387 A | 12/1992 | Kronner | |
| 5,231,974 A | 8/1993 | Giglio et al. | |

(Continued)

FOREIGN PATENT DOCUMENTS

| | | |
|---|---|---|
| DE | 10001695 | 2/2001 |
| DE | 102009014527 | 9/2010 |

(Continued)

OTHER PUBLICATIONS

EP Search Report 11 25 0163 dated Jun. 7, 2011.

(Continued)

*Primary Examiner* — Nicholas Woodall

(57) ABSTRACT

A surgical access assembly is disclosed that is configured and dimensioned for positioning within an opening in tissue providing access to and internal body cavity to facilitate the passage of a surgical instrument into an internal work site. The surgical access assembly includes first and second arms and third and fourth arms. The first and second arms and the third and fourth arms are configured and dimensioned for relative movement such that the surgical access assembly is reconfigurable between a first configuration, wherein a first transverse dimension is defined, and a second configuration wherein a second transverse dimension is defined. The first transverse dimension is smaller than the second transverse dimension.

20 Claims, 9 Drawing Sheets

(56) References Cited

U.S. PATENT DOCUMENTS

| | | |
|---|---|---|
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri et al. |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | De la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A * | 8/1999 | Taylor et al. ................. 606/198 |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | De la Torre et al. |
| 6,033,362 A | 3/2000 | Cohn |
| 6,033,425 A | 3/2000 | Looney et al. |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero |
| 6,312,377 B1 | 11/2001 | Segermark et al. |
| 6,331,158 B1 | 12/2001 | Hu et al. |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Herman et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | De la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0176771 A1 * | 9/2003 | Pulford et al. ................. 600/208 |
| 2003/0191371 A1 | 10/2003 | Smith et al. |
| 2004/0049099 A1 | 3/2004 | Ewers et al. |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149306 A1 | 7/2006 | Hart et al. |
| 2006/0155170 A1 | 7/2006 | Hanson et al. |
| 2006/1014913 | 7/2006 | Pingleton et al. |
| 2007/0027364 A1 | 2/2007 | Schwer |
| 2007/0073110 A1 | 3/2007 | Larson et al. |
| 2008/0132766 A1 | 6/2008 | Dant et al. |
| 2008/0234550 A1 | 9/2008 | Hawkes et al. |
| 2009/0204067 A1 | 8/2009 | Abu-Halawa |
| 2009/0265941 A1 | 10/2009 | Kurrus |
| 2009/0299148 A1 | 12/2009 | White et al. |
| 2010/0210916 A1 | 8/2010 | Hu et al. |
| 2010/0234689 A1 | 9/2010 | Wagner et al. |
| 2010/0261970 A1 | 10/2010 | Shelton, IV et al. |

FOREIGN PATENT DOCUMENTS

| | | |
|---|---|---|
| EP | 0177177 | 4/1986 |
| EP | 2179669 | 4/2010 |
| EP | 2 228 014 | 9/2010 |
| EP | 2228024 | 9/2010 |
| EP | 2 238 931 A1 | 10/2010 |
| EP | 2 417 922 | 2/2012 |

(56) References Cited

FOREIGN PATENT DOCUMENTS

| | | |
|---|---|---|
| GB | 2275420 | 8/1994 |
| WO | WO95/00197 | 1/1995 |
| WO | WO95/15715 | 6/1995 |
| WO | WO 01/08563 A2 | 2/2001 |
| WO | WO03/034908 | 5/2003 |
| WO | WO2005/089655 | 9/2005 |
| WO | WO 2010/136805 | 12/2010 |
| WO | WO 2011/079374 | 7/2011 |

OTHER PUBLICATIONS

EP Search Report 11 25 0164 dated Jun. 8, 2011.
EP Search Report EP 11 18 9987 dated Feb. 15, 2012.
EP Search Report EP 12160423.5 dated Jun. 25, 2012.
European Search Report EP 11 25 0719 dated Nov. 16, 2011.

* cited by examiner

EXPANDABLE SURGICAL ACCESS PORT

This application claims priority from provisional application Ser. No. 61/304,131, filed Feb. 12, 2010, the entire contents of which are incorporated herein by reference.

BACKGROUND

1. Technical Field

The present disclosure relates generally to devices and techniques for performing surgical procedures. More particularly, the present disclosure relates to an access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site therethrough through the passageway in the access assembly.

In the interests of facilitating visualization, the introduction of certain surgical instruments, and/or the removal of tissue specimens during minimally invasive thoracic procedures, it may be desirable to spread the adjacent ribs defining the intercostal space and/or retract soft tissue. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for thoracic access ports which minimize post operative patient pain while enabling atraumatic retraction of tissue and which do not restrict access to the body cavity.

SUMMARY

In the present disclosure, a surgical access assembly is disclosed that is configured and dimensioned for positioning within an opening in tissue providing access to an internal body cavity to facilitate the passage of a surgical instrument into an internal work site.

The surgical access assembly includes in one aspect first and second arms and third and fourth arms. The arms are configured and dimensioned for relative movement such that the surgical access assembly is reconfigurable between first and second configurations. In the first configuration, the access assembly defines a first transverse dimension, and in the second configuration, the access assembly defines a second transverse dimension, the first transverse dimension being smaller than the second transverse dimension.

The arms may each include arcuate distal portions and/or arcuate proximal portions that are configured and dimensioned to conform to a contour of the patient's tissue. In some embodiments, the arcuate distal portions and/or arcuate proximal portions curve in opposing directions.

The surgical access assembly may further include a flexible member extending between the arms, e.g., a sleeve member formed from a substantially compliant material, to facilitate enlargement of the opening in the patient's tissue during movement of the access assembly from the first configuration to the second configuration. The surgical access assembly may further include a rod extending between the first and third arms of the access assembly about which the flexible member may be positioned.

Additionally, or alternatively, the surgical access assembly may include a biasing member that is operatively associated with one of the first and second arms. The biasing member, in some embodiments, may normally bias the access assembly towards the first configuration, and in other embodiments towards the second configuration. A locking member can be provided to maintain the second configuration of the access assembly.

The access assembly may also include one or more cushioning members, preferably positioned adjacent a tissue contacting portion of the access assembly and preferably formed from a substantially compliant material.

In some embodiments, the first and second arms move in a scissor like movement and the third and fourth arms move in a scissor like movement to selectively reconfigure the access assembly between first and second configurations In another aspect of the present disclosure, a method of obtaining a tissue sample from within an internal surgical work site is disclosed. The method includes the steps of: (i) advancing an access assembly through an opening in tissue and into the intercostal space, wherein the access assembly includes first and second sections each having first and second arms; (ii) reconfiguring the access assembly via relative movement of the arms of the first and second sections to thereby enlarge the opening in the tissue; (iii) inserting a specimen retrieval instrument into the internal work site through a passageway extending through the access assembly; and (iv) utilizing the specimen retrieval instrument to obtain the tissue sample and withdraw it through the access assembly.

The step of reconfiguring the access assembly may include separation of the arms of the first and second members via a biasing member. The method may further include the step of reconfiguring the access assembly into a first configuration prior to the step of advancing the access assembly via application of an inwardly directed force to the first and second members to overcome a bias applied by a biasing member.

The method may further reconfiguring the access assembly by separation of the arms of the first and second members in a scissor like movement.

In some embodiments, the access assembly includes a flexible member and relative movement of the arms enables the flexible member to spread tissue adjacent the opening.

BRIEF DESCRIPTION OF THE DRAWINGS

Various exemplary embodiments of the present disclosure are described herein below with reference to the drawings, wherein.

DETAILED DESCRIPTION OF THE EMBODIMENTS

Figure 1:
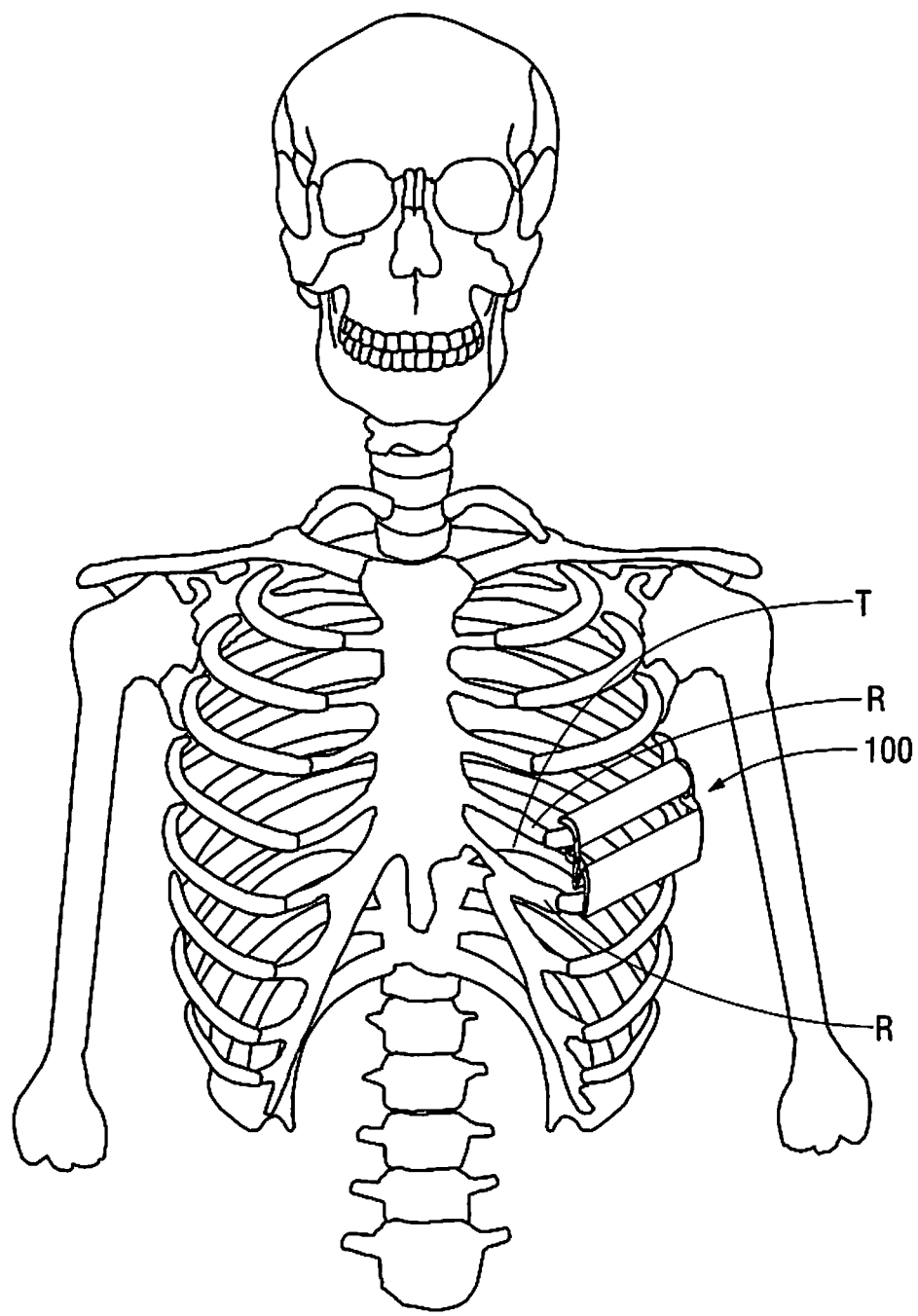
FIG. 1 is a front view illustrating a patient's skeletal structure with one embodiment of the presently disclosed surgical access assembly positioned within the intercostal space defined between adjacent ribs.

Various embodiments of the presently disclosed access assembly, and methods of using the same, will now be described in detail with reference to the drawings wherein like references numerals identify similar or identical elements. In the drawings, and in the following description, the term "proximal" should be understood as referring to the end of the access assembly, or component thereof, that is closer to the clinician during proper use, while the term "distal" should be understood as referring to the end that is farther from the clinician, as is traditional and conventional in the art. Additionally, use of the term "tissue" herein below should be understood to encompass both the patient's ribs, and any surrounding tissues. It should be also be understood that the term "minimally invasive procedure" is intended to include surgical procedures through small openings/incisions performed within a confined space such as the thoracic cavity or abdominal cavity.

Figure 2:
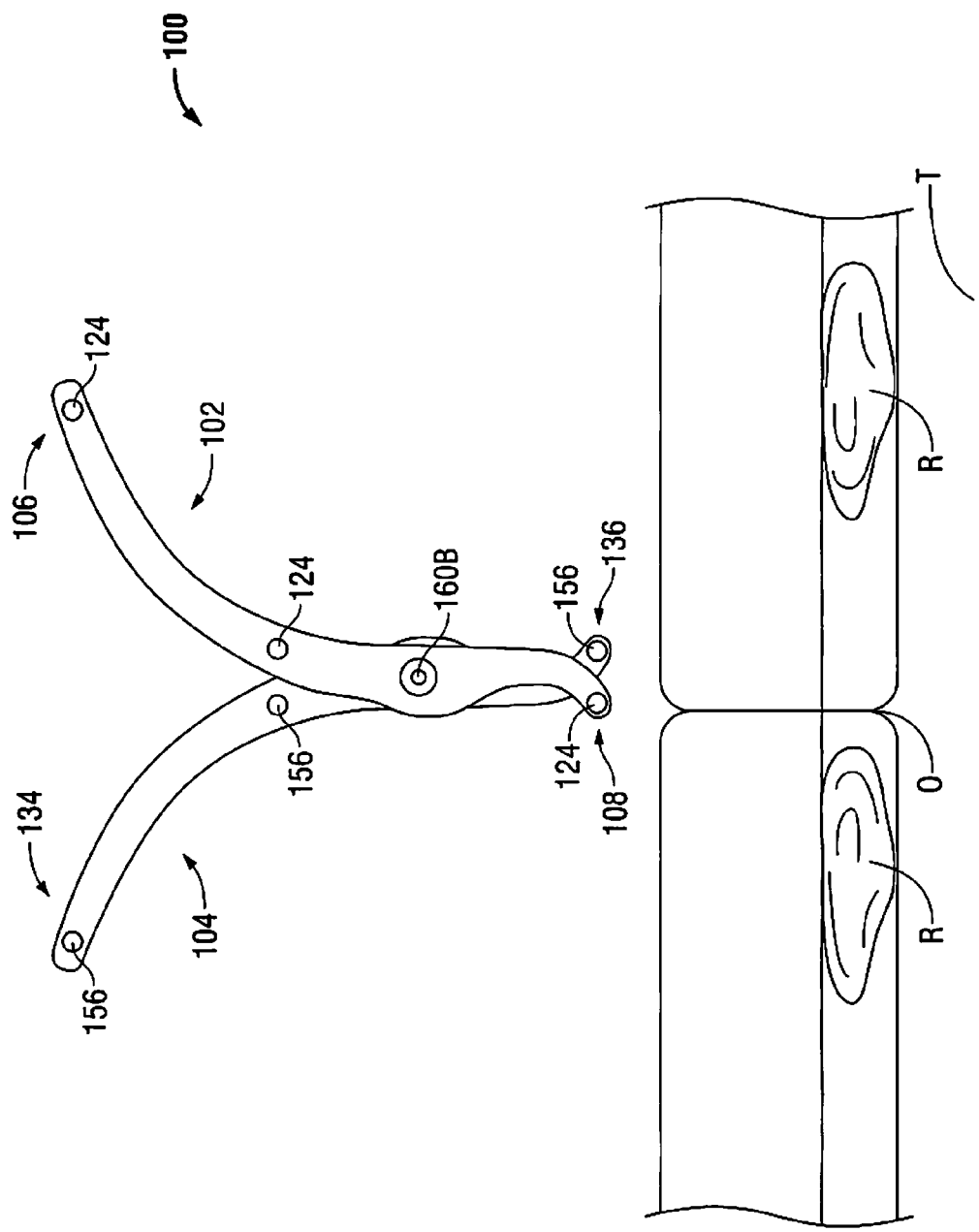
FIG. 2 is a side view of the surgical access assembly of FIG. 1 prior to insertion into an opening in the patient's tissue.

FIGS. 1-6 illustrate one embodiment of the presently disclosed surgical access assembly, identified by the reference numeral 100, in use for a minimally invasive thoracic surgical procedure. It should be appreciated that the surgical access assembly 100 (and the other access assemblies disclosed herein) can also be utilized to access other body cavities in other minimally invasive procedures. The access assembly 100 is depicted as a thoracic port configured and dimensioned for insertion into the intercostal space "T" located between a patient's adjacent ribs "R" through an opening or incision "O" (FIG. 2) in the tissue for the insertion of instruments therethrough for manipulation within the thoracic cavity (FIGS. 1, 2). The various components of the access assembly 100 may be formed from any suitable biocompatible material, including, but not limited to, polymeric materials.

The access assembly 100 includes a first section 102 and a second section 104. The first section 102 includes respective proximal and distal ends 106, 108 (FIG. 2), a first arm 110 (FIG. 3), a second arm 112, and a flexible member such as a sleeve member, or sheath, 114 that extends transversely between the arms 110, 112 from the proximal end 106 of the first section 102 to the distal end 108.

The arms 110, 112 of the first section 102 are each formed from a substantially rigid, biocompatible material, including for example, metallic materials such as stainless steel and titanium alloys and non-metallic materials include polymers and co-polymers such as Acetal resin, ABS and LCP. The arms 110, 112, respectively include arcuate proximal portions 116, 118 and distal portions 120, 122. The curvature at the proximal portion 116 of the first arm 110 is opposite the curvature at the proximal portion 118 of the second arm 112, and the curvature at the distal portion 120 of the first arm 110 is opposite the curvature at the distal portion 122 of the second arm 112.

The sleeve (e.g. membrane) 114 (FIG. 3) may be formed from a flexible, compliant material, such as polyurethane, polyisporene, silicone rubber and TPE (thermoplastic elastomer such as DuPont Hytrel), to allow for deflection and deformation of the sleeve 114 when in contact with tissue, e.g., to protect nerve and muscle tissue, or alternatively, the sleeve 114 may be substantially more rigid in structure in the form of for example a rigid plate to provide a greater spreading force on the ribs. In the embodiment illustrated in FIGS. 1-6, the sleeve 114 is supported by one or more rods 124 extending between the first section 102 and the second section 104. In the illustrated embodiment, three rods 124 are provided. It is envisioned that the rods 124 may be integrally formed with the respective first and second members 102, 104, e.g., monolithically formed, or attached via the use of an adhesive, or mechanically coupled to the respective first and second members 102, 104, e.g., via the use of threaded engagement structure or a snap fit. In the embodiment of the access assembly 100 illustrated in FIGS. 1-6, the sleeve 114 is configured as a band 126 (FIG. 3) defining one or more interior spaces 128 through which the rods 124 pass. It is also envisioned, however, that opposing ends 130, 132 of the sleeve member 114 may be secured to proximal-most and distal-most rods 124 such as by an adhesive.

The second section 104 of the access assembly 100 includes respective proximal and distal ends 134, 136 (FIG. 2), a first arm 138 (FIG. 3), a second arm 140, and a flexible member such as a sleeve member, or sheath, 142, that extends laterally between the arms 138, 140 from the proximal end 134 of the second section 104 to the distal end 136. As used herein, the first and second arms 138 and 140 of the second section 104 can also be considered "third and fourth arms", respectively.

As with the first and second arms 110, 112 of the first section 102, the first and second arms 138, 140 of the second section 104 are each formed from a substantially rigid, biocompatible material, such as the materials listed above for arms 110, 112. The arms 138, 140, respectively include arcuate proximal portions 144, 146 and arcuate distal portions 148, 150. The curvature at the proximal portion 144 of the first arm 138 is opposite that of the proximal portion 146 of the second arm 140, and the curvature at the distal portion 148 of the first arm 138 is opposite that of the distal portion 150 of the second arm 140.

The arcuate configurations of the arms 110, 112 included at the proximal portions 116, 118 and distal portions 120, 122 and the arcuate configurations of the arms 138, 140 included at the proximal portions 144, 146 and distal portions 148, 150 thereof, respectively, allow the first and second sections 102, 104 to conform to the contour of the patient's tissue during use, thereby increasing reliability regarding placement of the access assembly 100, and the ability of the access assembly 100 to withstand forces that are applied during manipulation of any surgical instrument(s) inserted therethrough.

The sleeve (e.g. membrane) 142 (FIG. 3) of the second section 104 may be formed from a flexible, compliant material, such as the materials listed above for sleeve member 114, to allow for deflection and deformation of the sleeve 142 when in contact with tissue, e.g., to protect nerve and muscle tissue, or alternatively, the sleeve 142 may be substantially more rigid in structure in the form for example of a rigid plat for spreading the ribs. In the embodiment illustrated in FIGS. 1-6, the sleeve 142 is configured as a band 152 (FIG. 3) defining one or more interior spaces 154 that accommodate rod(s) 156 (FIGS. 2, 3) extending between the first section 102 and the second section 104. In the illustrated embodiment, three rods 156 are provided. The rods 156 can be integrally formed, e.g. monolithically formed, or attached via adhesive or mechanically coupled as in rods 124. It is also envisioned that opposing ends 158, 160 of the sleeve member 142 may be secured to the proximalmost and distalmost rods 156, e.g., via an adhesive.

The configuration and dimensions of the first section or member 102 (FIG. 3) may be identical to those of the second section or member 104 in order to reduce costs associated with manufacture, and increase the ease of assembly. Alternatively, however, the configuration and dimensions of the first member 102 may differ from those of the second member 104.

Figure 3:
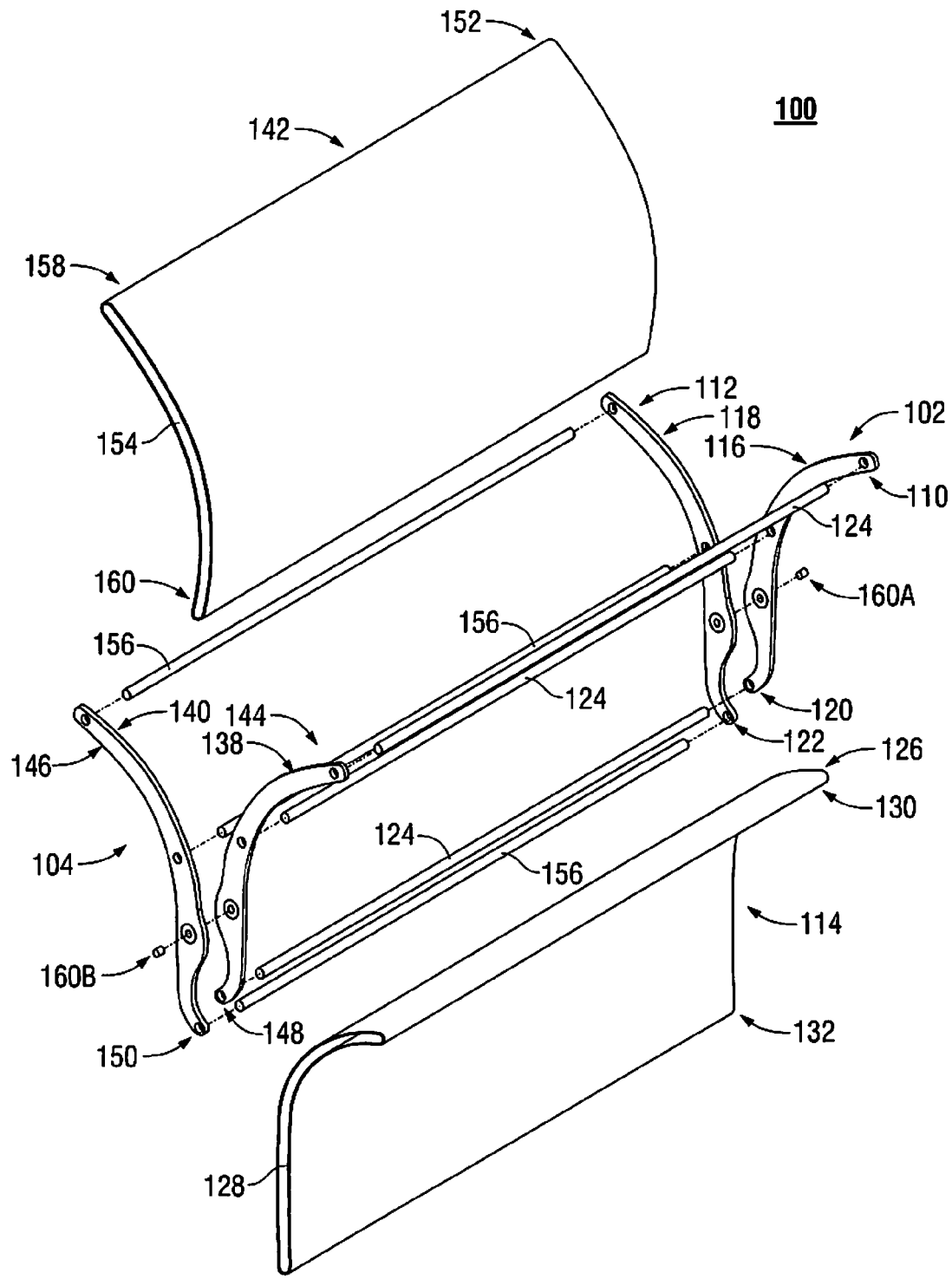
FIG. 3 is a top, perspective view of the surgical access assembly with parts separated.
Figure 4:
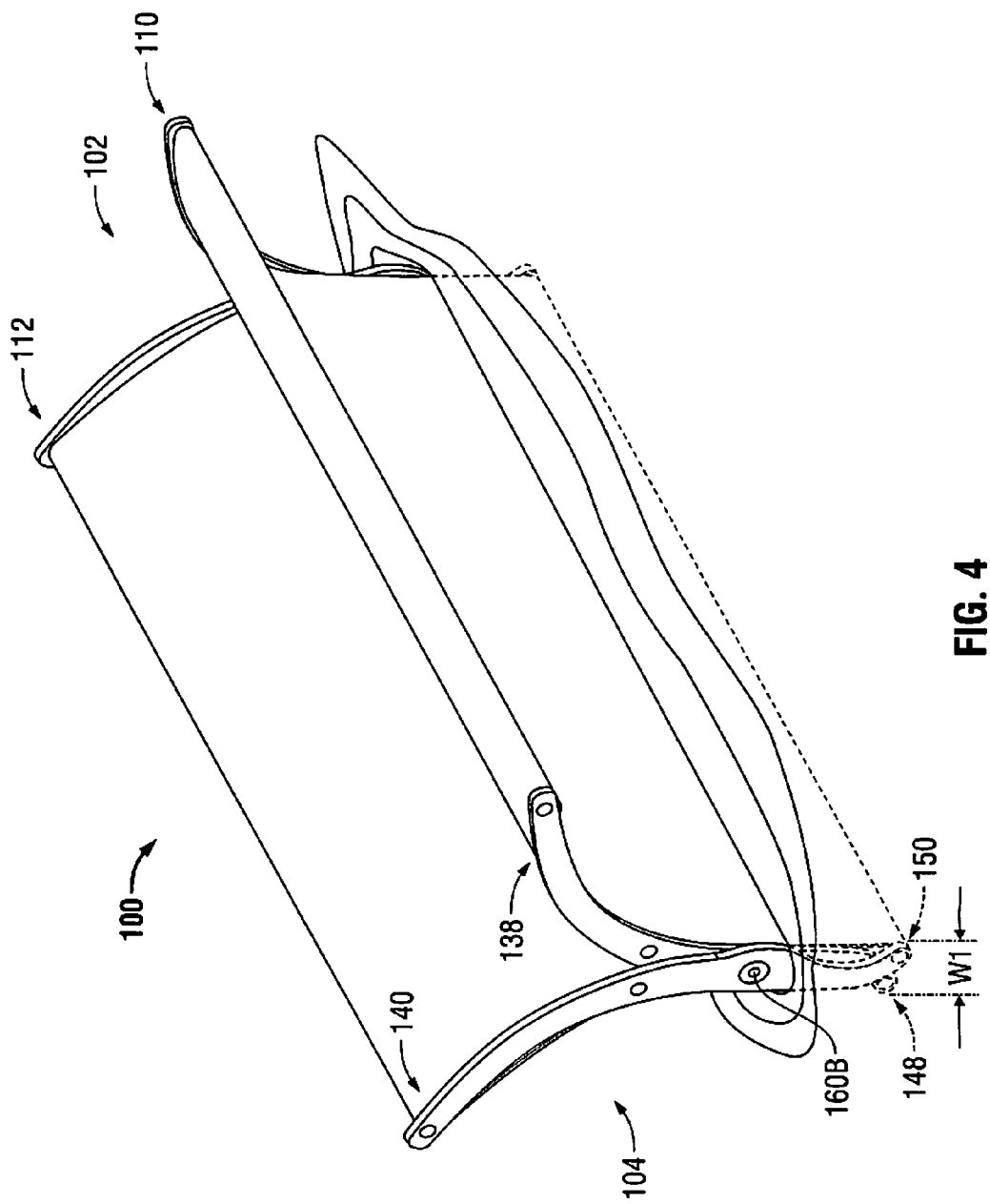
FIG. 4 is a top, perspective view of the surgical access assembly shown in a collapsed configuration and positioned within the opening in the patient's tissue.
Figure 5:
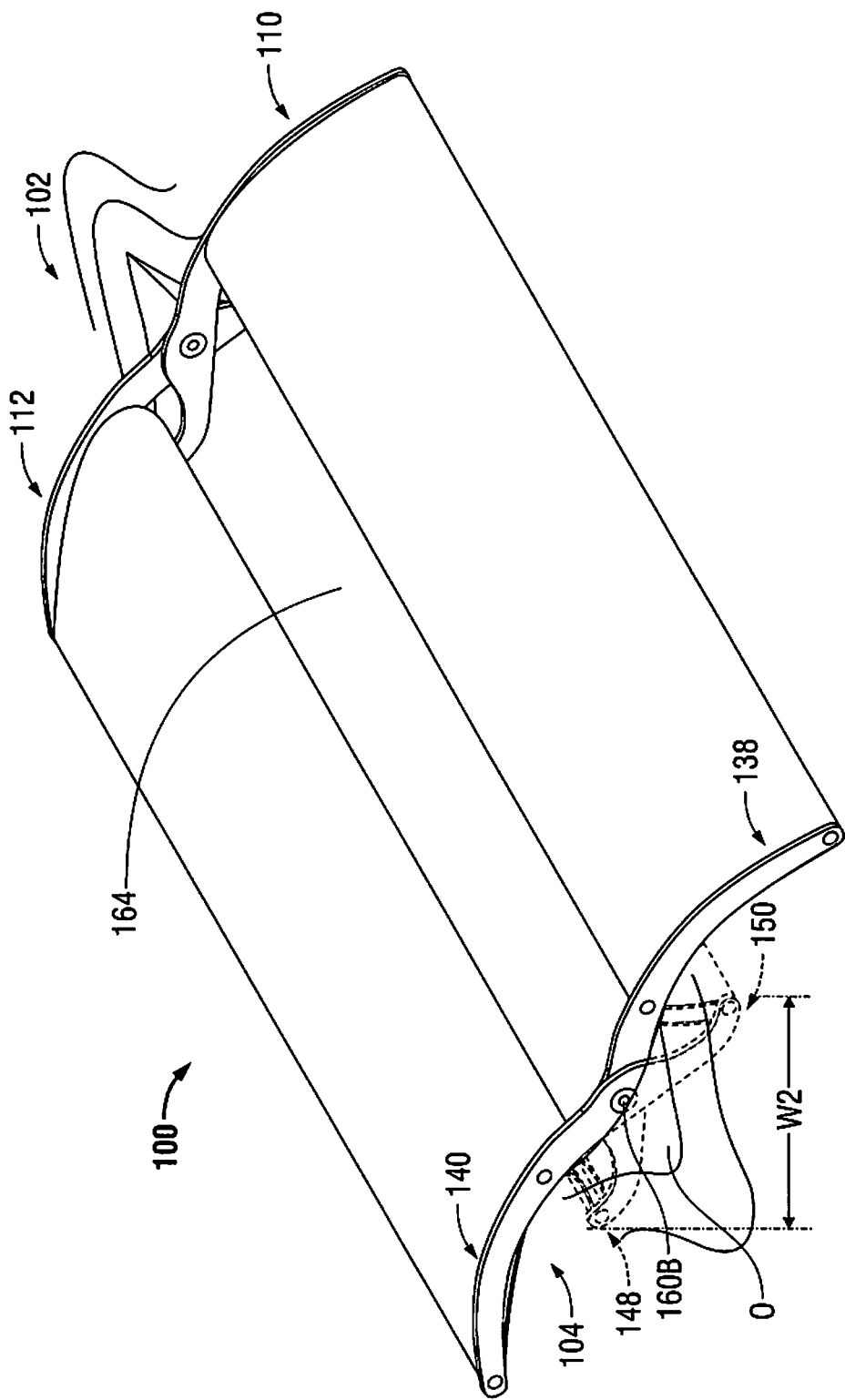
FIGS. 5 and 6 are top, perspective views of the surgical access assembly shown in an expanded configuration following insertion into the opening in the patient's tissue.
Figure 6:
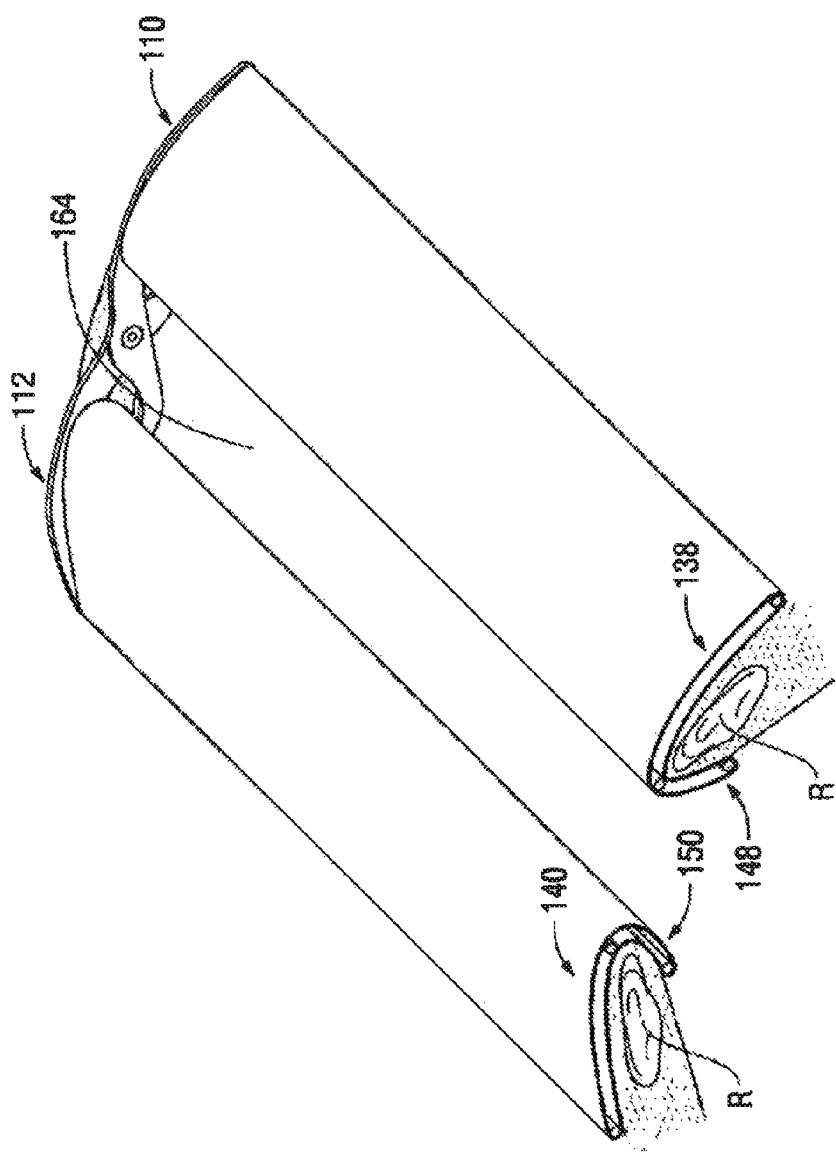

As best seen in FIG. 3, the arms 110, 112 are pivotally connected via a pivot member 160A and the arms 138, 140 are pivotally connected via a pivot member 160B. The pivot members 160A, 160B allow for movement of the access assembly 100 between a first, collapsed configuration (FIG. 4), and a second, expanded configuration (FIGS. 5 and 6). Additionally, providing a pivot point on each transverse end of the access assembly 100 not only minimizes obstruction regarding instrument insertion, but allows each end of the access assembly 100 to move independently of the other. Allowing the transverse ends of the access assembly 100 to move independently of each other inhibits movement of the access assembly 100 during manipulation of the surgical instrument(s) inserted therethrough, e.g., movement that may otherwise occur due to instrument torquing.

In the collapsed configuration (FIG. 4), the respective first and second sections or members 102, 104 of the access assembly 100 are in an approximated position such that the access assembly 100 assumes a reduced profile defining a smaller transverse dimension than in the expanded configuration. The reduced transverse dimension facilitates atraumatic insertion and removal of the access assembly 100. Specifically, in the collapsed configuration, the access assembly 100 defines a width "W1" (FIG. 4) measured between the distal portions of the aims of the first and second members 102, 104, e.g., between the respective distal portions 148, 150 of the arms 138, 140, whereas in the expanded configuration, the access assembly 100 defines a larger width "W2" (FIG. 5).

During the course of a thoracic surgical procedure, in the collapsed configuration, the access assembly 100 is positioned between the patient's adjacent ribs "R" (FIG. 2) through the opening "O" formed in the tissue. During expansion of the access assembly 100, the first and second members 102, 104 are spread apart by spreading apart arms 110, 112 and aims 138, 140 so as to define a passageway 164 (FIGS. 5, 6) extending through the access assembly 100, and dilate the opening "O" (FIGS. 2, 5). Spreading the tissue to dilate the opening "O" facilitates access to the thoracic cavity located beneath the tissue, and facilitates the insertion and removal of surgical instrumentation, as well as the removal of tissue from the thoracic cavity.

To move the access assembly 100 from the collapsed configuration (FIG. 4) to the expanded configuration (FIGS. 5, 6), the arms 110, 112 of the first member 102 and the arms 138, 140 of the second member 104 are separated by the user separating the arcuate proximal portions 116, 118. To move the access assembly 100 from the expanded configuration (FIGS. 5, 6) to the collapsed configuration (FIG. 4) the aims 110, 112 of the first member 102 and the arms 138, 140 of the second member 104 are moved toward each other. The pivotal connections between the arms 110, 112 and between the arms 138, 140 established by the pivot members 160A, 160B, respectively, allows for scissor-like movement of the access assembly 100 during movement between the collapsed and expanded configurations.

With continued reference to FIGS. 1-6, use and operation of the access assembly 100 will be discussed during the course of a minimally invasive surgical procedure. While the access assembly 100 will be discussed in the context of a thoracic procedure, it should be appreciated that the following discussion of the access assembly 100 is applicable to other minimally invasive surgical procedures.

Initially, the opening "O" (FIG. 2) is made in the outer tissue wall of the thoracic cavity "T". Thereafter, with the access assembly 100 in the collapsed configuration (FIG. 4), the clinician inserts the access assembly 100 into the opening "O," and positions the access assembly 100 in the intercostal space between adjacent ribs "R." Specifically, the access assembly 100 is oriented such that the arcuate distal portions 120, 122 (FIG. 3) of the arms 110, 112, and arcuate distal portions 148, 150 (FIGS. 3, 6) of the arms 138, 140 are positioned for engagement with the patient's tissue upon expansion.

Following placement as desired, the access assembly 100 is expanded. During expansion, the proximal portions of arms 110, 112 and arms 138, 140 are moved apart, thereby moving the respective distal portions 120, 122 (FIG. 3) of the arms 110, 112 and the respective distal portions 148, 150 (FIGS. 3, 6) of the arms 138, 140 in opposing directions to thereby spread the tissue adjacent the ribs to dilate the opening "O" (FIGS. 2, 5).

It is noted that the access assembly 100 may be configured and dimensioned in some embodiments such that relative movement between the arms 110, 112 of the first section 102 and relative movement between the arms 138, 140 of the second section 104 may also separate the patient's ribs "R," if necessary or desired, in order to further increase the clinician's access to the thoracic cavity "T."

With particular reference to FIGS. 5 and 6, after dilation of the opening "O" in the tissue, the clinician carries out the remainder of the surgical procedure by passing one or more surgical instruments (not shown) through the passageway 164 defined between the respective first and second sections 102, 104 when the access assembly 100 is in the expanded configuration.

The surgical instrument(s) inserted through the access assembly 100 may be any surgical instrument(s) configured and dimensioned to pass through the passageway 164 extending through the access assembly 100, and adapted to perform a surgical, diagnostic, or other desired procedure. For example, suitable surgical instruments may include endoscopic apparatus, which perform a variety of functions such as the application of surgical clips or other such fasteners, the cutting of body tissue, and/or specimen retrieval for removing an internal tissue sample.

In order to facilitate passage of the surgical instrument(s) into the thoracic cavity "T," and/or removal of the surgical instrument(s) therefrom, as well as to facilitate withdrawal of tissue specimens therethrough, it is envisioned that surgical instrument(s), and/or the inner surfaces of the access assembly 100 defining the passageway 164 extending therethrough, may be partially, or entirely, coated with a biocompatible, lubricous material.

Following completed use of the surgical instrument(s), the instrument(s) are withdrawn from the access assembly 100, and the access assembly 100 is returned to the collapsed configuration. As mentioned above, the reduced profile of the access assembly 100 in the collapsed configuration allows for atraumatic removal of the access assembly 100 from the intercostal space.

It should be appreciated that tension in the sleeves 114, 142 can maintain the access assembly in the open position while inserted in the patient cavity. However, it should also be appreciated that locking members are also contemplated to maintain the assembly in the open position.

Figure 7:
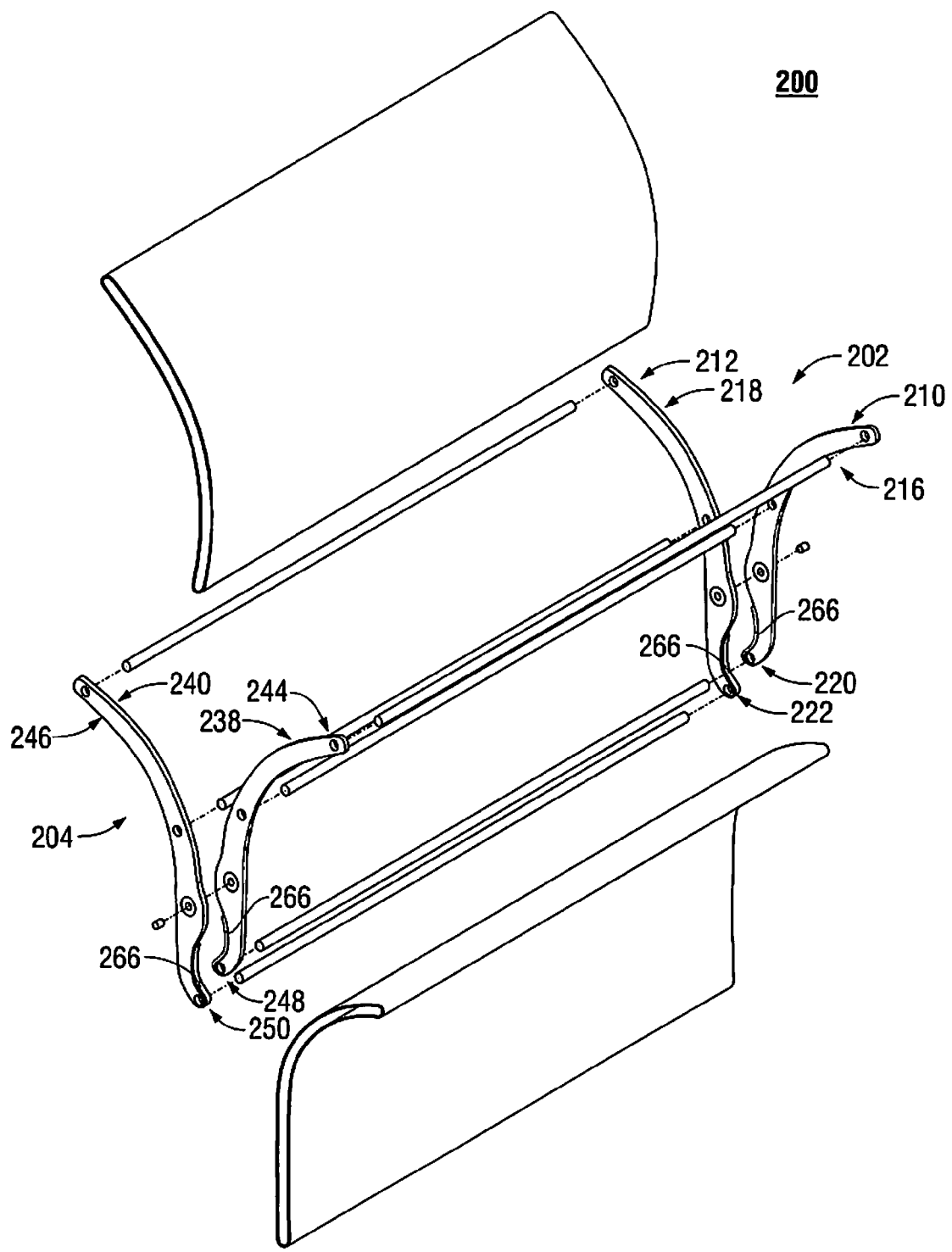
FIG. 7 is a top, perspective view of an alternative embodiment of the presently disclosed surgical access assembly with parts separated.
Figure 8:
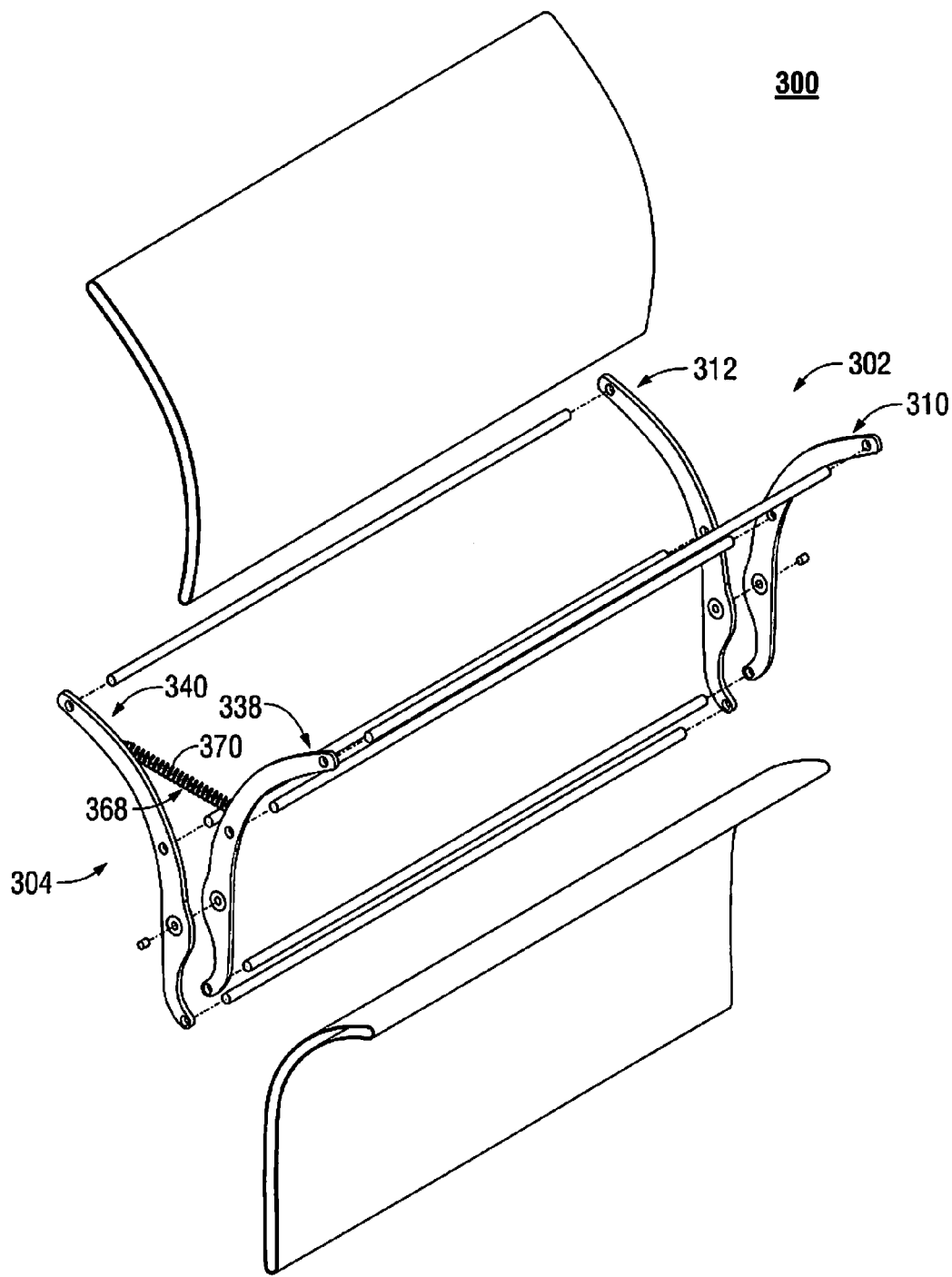
FIG. 8 is a top, perspective view of another embodiment of the presently disclosed surgical access assembly with parts separated.
Figure 9:
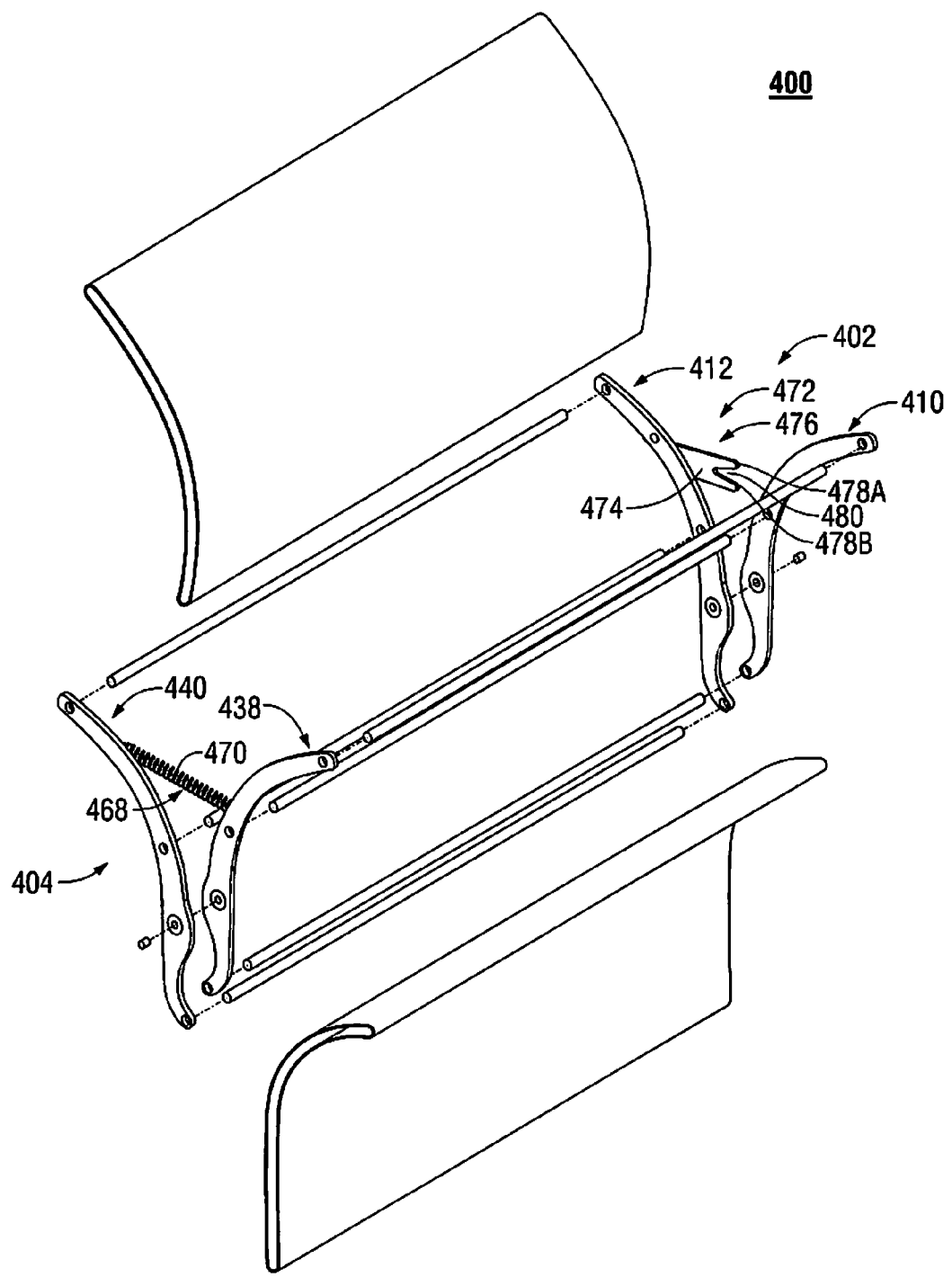
FIG. 9 is a top, perspective view of yet another embodiment of the presently disclosed surgical access assembly with parts separated.

With reference now to FIGS. 7-9, alterative embodiments of the presently disclosed access assembly will be discussed. Each embodiment disclosed herein below is substantially similar to the access assembly 100 discussed above with respect to FIGS. 1-6, and accordingly, will only be discussed with respect to any differences therefrom. Thus, the arms of these embodiments operate in the same manner as arms 110, 112, 138 and 140 of the FIG. 1 embodiment to spread and collapse the access assembly.

FIG. 7 illustrates an embodiment of the presently disclosed access assembly that is identified by the reference numeral 200. The access assembly 200 includes a first section or member 202 with arms 210, 212 having arcuate proximal portions 216, 218 and arcuate distal portions 220, 222, respectively, and a second member or section 204 with arms 238, 240 having arcuate proximal portions 244, 246 and arcuate distal portions 248, 250.

The arms 210, 212 of the first section 202, and the arms 238, 240 of the second member 204 each include one or more cushioning portions 266 on an internal surface that are formed from a material that is relatively soft and compliant when compared to the material comprising the arms 210, 212, 238, 240 themselves. The cushioning portions 266 are positioned adjacent portions of the access assembly 100 that come into contact with the patient's tissue during use in order to protect the nerves and other tissue, thereby reducing patient discomfort and post-operative pain as well as reducing tissue trauma and/or overall recovery time.

Although the cushioning portions 266 are illustrated solely in association with the arcuate distal portions 220, 222 of the first member 202 and the arcuate distal portions 248, 250 of the second member 204 in FIG. 7, in alternative embodiments, it is envisioned that the cushioning portions 266 may be larger in size, or present in greater numbers. For example, additional cushioning portions 266 may be positioned within the curvature defined by the proximal portions 216, 218 of the arms 210, 212 202, and the proximal portions 244, 246 of the arms 238, 240.

FIG. 8 illustrates another embodiment of the presently disclosed access assembly that is identified by the reference character 300. The access assembly 300 includes a first member or section 302 with arms 310, 312, a second section or member 304 with arms 338, 340, and a biasing member 368.

The biasing member 368 is configured such that absent the influence of any external forces, the access assembly 300 will realize the expanded configuration (as in FIG. 5). The biasing member may be any structure suitable for this intended purpose, e.g., a spring 370 or a flexible membrane (not shown) spanning arms 338, 340 or spanning the sleeve members wherein tension in the membrane holds the arms open and opens the sleeve members or plates. In the embodiment of the access assembly 300 illustrated in FIG. 8, the biasing member 368 is positioned between the arms 338, 340 of the second member 304. However, the specific position of the biasing member 368 may be varied in alternative embodiments of the access assembly 300 without departing from the scope of the present disclosure. For example, it is envisioned that the biasing member 368 may be positioned between the arms 310, 312 of the first member 302 or both pairs of arms 338, 340 and 310, 312 can have a biasing member. To move the access assembly to the collapsed position for insertion into the body cavity (and for subsequent withdrawal), the respective arms 338, 340 and 310, 312 are pushed together by the user (at their proximal portions) to overcome the bias of spring 370. Once inside the body cavity, the user releases the arms 338, 340 and 310, 312, causing the arms to move to their biased spread position.

FIG. 9 illustrates yet another embodiment of the presently disclosed access assembly that is identified by the reference character 400. The access assembly 400 includes a first section or member 402 with arms 410, 412, a second section or member 404 with arms 438, 440, a biasing member 468, and a locking member 472.

Whereas the biasing member 368 of the access assembly 300 of FIG. 8 normally biases the access assembly 300 towards the expanded configuration (FIG. 5), the biasing member 468 included on the access assembly 400 normally biases the access assembly 400 towards the collapsed configuration (as in FIGS. 2, 4), and may be any structure suitable for this intended purpose, such as a spring (FIG. 9) or a flexible membrane (not shown) spanning the arms 438, 440 or the sleeve members or plates.

Upon overcoming the bias provided by the biasing member 468 to realize the expanded configuration, i.e., through the application of an external force to the respective arms of the first and second sections or members 402, 404 of the access assembly 400 to spread the arms, the locking member 472 is actuated via movement into a position whereby approximation of the first member 402 and the second member 404 is inhibited in order to maintain the expanded configuration of the access assembly 400.

In the specific embodiment of the access assembly 400 shown in FIG. 9, the locking member 472 is illustrated as including a lever 474 that is pivotally connected to the first member 402. The lever 474 includes a Y-shaped portion 476 with branches 478A, 478B defining a space 480 therebetween that is configured and dimensioned for engagement with the arm 410, e.g. engagement with a projection on arm 410, to thereby inhibit continued approximation of the arms 410, 412 as the proximal portions cannot be moved toward each other. It should be appreciated, however, that the locking member 472 may assume any configuration or dimensions, and/or may be positioned in any location, suitable for the intended purpose of maintaining the expanded configuration of the access assembly 400. For example, rather than being pivotally connected to the first member 402, the locking member 472 may alternatively be connected to the second arm 404. Locking members can also be placed on both sections 402, 404 and a biasing member can be placed on one or both pairs of arms.

Persons skilled in the art will understand that the structures and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical access assembly configured and dimensioned for positioning within an opening in tissue providing access to an internal body cavity, the surgical access assembly comprising a passageway defining a longitudinal axis for passage of a surgical instrument into an internal work site, first and second arms, and third and fourth arms, the first and second arms and the third and fourth arms being configured and dimensioned for relative movement such that the surgical access assembly is reconfigurable between a first configuration, wherein a first transverse dimension is defined, and a second configuration, wherein a second transverse dimension is defined, the first transverse dimension being smaller than the second transverse dimension, the first and second arms being connected at a first point, and the third and fourth arms being connected at a second point such that the distance between the first and second points along the longitudinal axis remains constant during movement of the surgical access assembly between the first and second configurations, the access assembly further including a flexible member connected to at least one of the arms, the flexible member facilitating enlargement of the opening in the tissue during movement of the access assembly from the first configuration to the second configuration.

2. The surgical access assembly of claim 1, wherein the first and second arms are pivotally connected at the first point and the third and fourth arms are pivotally connected at the second point.

3. The surgical access assembly of claim 1, wherein the first and second arms and the third and fourth arms each include arcuate distal portions configured and dimensioned to conform to a contour of the tissue.

4. The surgical access assembly of claim 3, wherein the arcuate distal portions of the first and second arms curve in opposing directions, and the arcuate distal portions of the third and fourth arms curve in opposing directions.

5. The surgical access assembly of claim 1, wherein the first and second arms and the third and fourth arms each include arcuate proximal portions configured and dimensioned to conform to a contour of the tissue.

6. The surgical access assembly of claim 5, wherein the arcuate proximal portions of the first and second arms curve in opposing directions, and the arcuate proximal portions of the third and fourth arms curve in opposing directions.

7. The surgical access assembly of claim 1, wherein the flexible member is formed from a substantially compliant material.

8. The surgical access assembly of claim 1, further including a rod extending between the first and third arms, the flexible member being positioned about the rod.

9. The surgical access assembly of claim 1, wherein the first and second arms are positioned on an opposing side of the access assembly from the third and fourth arms, the first and second arms further comprising first and second flexible members supported between the opposing arms.

10. The surgical access assembly of claim 1, further including a biasing member operatively associated with one of the first and second arms, the biasing member configured and dimensioned to normally bias the access assembly towards the first configuration.

11. The surgical access assembly of claim 1, further including a locking member operatively associated with one of the first and second arms, the locking member positioned for selective actuation to maintain the second configuration of the access assembly.

12. The surgical access assembly of claim 1, further including a biasing member operatively associated with one of the first and second arms, the biasing member being configured and dimensioned to normally bias the access assembly towards the second configuration.

13. The surgical access assembly of claim 1, further including a cushioning member positioned adjacent a tissue contacting portion of the access assembly, the cushioning member being formed from a substantially compliant material.

14. The surgical access assembly of claim 1, wherein a cushioning material is positioned on at least the first and third arms.

15. The surgical access assembly of claim 1, wherein the first and second members move in a scissor-like movement to selectively move the access assembly between the first and second configurations.

16. The surgical access assembly of claim 15, wherein the third and fourth members move in a scissor-like movement to selectively move the access assembly between the first and second configurations.

17. A surgical access assembly comprising:
    a first member including a first pair of arms having proximal and distal ends; and
    a second member including a second pair of arms having proximal and distal ends, the surgical access assembly including a passageway defining a longitudinal axis configured to receive a surgical instrument, and being reconfigurable between an initial position, wherein the proximal ends of the first pair of arms define a first distance therebetween and the distal ends of the first pair of arms define a second distance therebetween, and a subsequent position, wherein the proximal ends of the first pair of arms define a third distance therebetween and the distal ends of the first pair of arms define a fourth distance therebetween, the first distance being greater than the third distance, and the fourth distance being greater than the second distance, the access assembly further including a flexible member connected to at least one of the pair of arms, the flexible member facilitating enlargement of the opening in the tissue during movement of the access assembly from the initial position to the subsequent position.

18. The surgical access assembly of claim 17, wherein the first pair of arms are connected to each other, and the second pair of arms are connected to each other such that the passageway is enlarged upon movement of the surgical access assembly from the initial position to the subsequent position.

19. The surgical access assembly of claim 18, wherein the first pair of arms are pivotally connected to each other, and the second pair of arms are pivotally connected to each other.

20. The surgical access assembly of claim 19, wherein the first and second arms are connected at a first pivot point, and the third and fourth arms are connected at a second pivot point such that the distance between the first and second points along the longitudinal axis remains constant during movement of the surgical access assembly between the first and second configurations.

* * * * *